(12) United States Patent
Bear (10) Patent No.: US 11,273,010 B2
(45) Date of Patent: Mar. 15, 2022

(54) OROFACIAL APPARATUSES AND METHODS

(71) Applicant: Johnny R. Bear, Marrero, LA (US)

(72) Inventor: Johnny R. Bear, Marrero, LA (US)

(73) Assignee: Johnny R. Bear, Marrero, LA (US)

( * ) Notice: Subject to any disclaimer, the term of this patent is extended or adjusted under 35 U.S.C. 154(b) by 544 days.

(21) Appl. No.: 16/040,143

(22) Filed: Jul. 19, 2018

(65) Prior Publication Data

US 2020/0022785 A1    Jan. 23, 2020

(51) Int. Cl.
*A61C 7/08*    (2006.01)
*A61C 7/20*    (2006.01)

(52) U.S. Cl.
CPC . *A61C 7/08* (2013.01); *A61C 7/20* (2013.01)

(58) Field of Classification Search
USPC ............................................................ 433/6
See application file for complete search history.

(56) References Cited

U.S. PATENT DOCUMENTS

| | | | | |
|---|---|---|---|---|
| 4,718,662 A | * | 1/1988 | North | A63B 23/032 128/860 |
| 4,997,182 A | * | 3/1991 | Kussick | A61F 5/58 128/861 |
| 5,052,409 A | * | 10/1991 | Tepper | A61F 5/566 128/859 |
| 5,376,001 A | * | 12/1994 | Tepper | A61C 7/00 433/6 |
| 8,062,031 B2 | * | 11/2011 | Inman | A61C 7/10 433/18 |
| 2005/0069834 A1 | * | 3/2005 | Inman | A61C 7/10 433/18 |
| 2011/0269095 A1 | * | 11/2011 | Singh | A61C 7/10 433/24 |
| 2014/0332011 A1 | * | 11/2014 | Turek | A61F 5/566 128/848 |
| 2017/0224987 A1 | * | 8/2017 | Kent | A61B 5/0826 |
| 2020/0022785 A1 | * | 1/2020 | Bear | A61F 5/566 |

* cited by examiner

*Primary Examiner* — Matthew M Nelson
(74) *Attorney, Agent, or Firm* — Adams and Reese LLP; Ray R. Ferrera (57) ABSTRACT

An example embodiment of the present disclosure provides a sublingual dental appliance for treatment of Orofacial Myofunctional Disorders (OMDs). The sublingual dental appliance may be a semi-permanent physical training device that guides the tongue into the appropriate position in the mouth, thereby training the muscles to address a disorder. The sublingual device may feature a pair of support structures that guide the tongue into the appropriate relationship with the palate, with the tongue directed in a superior angle to the superior portion of the mouth, against the hard palate, during both use and rest. Although the appliance may be semi-permanently affixed to the individual, the support structures of the appliance are directly affixed to flexible, adjustable elements that may be adjusted during use to reconfigure the angle or position of the support structures as needed during treatment.

12 Claims, 7 Drawing Sheets

OROFACIAL APPARATUSES AND METHODS

BRIEF DESCRIPTION OF DRAWINGS

Various aspects and features of the present disclosure are described herein with reference to the drawings, wherein like numerals refer to similar or identical elements and.

DESCRIPTION OF EMBODIMENTS

The present disclosure relates to orofacial apparatuses and methods, including sublingual apparatuses and methods for treating Orofacial Myofunctional Disorders (OMDs), as well as disorders related to the face and mouth. Embodiments include a dental device having a curved frame configured to align with a curve of the lower dental arch or mandible of the user, and a pair of adjustment pads affixed to a set of positioning arms extending from the curved frame. In use, the adjustment pads, which are applied under the tongue, guide the tongue to its appropriate position in relation to the palate. In embodiments, the apparatus may be used to retrain the muscles associated with OMDs.

Embodiments of the present disclosure can be used to treat tongue thrust, an OMD that can result in spaces between the teeth of an individual, open bites, or other facial abnormalities. Tongue thrust often results from a person swallowing incorrectly, with the top or sides of the tongue pressing against and spreading between the teeth. In such a situation, wherein the tongue is pushed against or between the teeth when swallowing, the tongue is "thrust" away from the hard palate of the individual. Open bites will result from the constant pressure on the lingual, or back, side of the upper and lower teeth, preventing the teeth from achieving their normal or desired positional relationship to each other. Skeletal change is likely to occur if this condition continues without adjustment. Abnormal muscle function will shift the position of teeth as well as bone, and improper alignment between the upper and lower teeth of an individual will, in turn, result in difficulties in biting or chewing food. It can also result in cosmetic issues, temporal mandibular joint ("TMJ") issues through added pressure to the TMJ, and speech issues such as lisping and the inability to form normal sound due to the abnormal positioning of the tongue.

Embodiments of the present disclosure provide for a physical training device that guides the tongue into the appropriate position in the mouth, thereby training muscles associated with a facial disorder without constant conscious exercise or use of punitive, painful devices. The sublingual (i.e., applied under the tongue) device features a pair of support structures that guide the tongue into the appropriate relationship with the palate. Instead of allowing the tongue to traverse the palate, the tongue is instead directed in a superior angle to the superior portion of the mouth, against the hard palate, during both use and rest. The device may, in some embodiments, be semi-permanently affixed to the individual, such that once it is applied, the device may stay in place for an elongated period of time, such as one year or longer, while treatment is ongoing. In preferred embodiments, the device may be cemented to certain teeth of the lower dental arch of the individual. However, the support structures of the sublingual appliance are directly affixed to flexible, adjustable elements that may be adjusted during use to reconfigure the angle or position of the support structures as needed during treatment. For example, in early stages of treatment, the support structures may be angled to apply minimal pressure to the ventral surface of the tongue, whereas in later stages of treatment the support structures may be angled in a manner that causes increased pressure to the ventral surface of the tongue, or at times, a posterior pressure at the base of the tongue.

The device may be affixed to the patient via one or more securing elements, which are secured or cemented to the teeth on the lower jaw of the user. The securing elements may be securing bands as conventionally used in dental apparatuses. In some embodiments, depending upon the age of treatment, the bands may each be secured to the lower molar teeth of the user. In some embodiments, additional stability elements may be placed on the lingual surfaces of additional teeth of the patient, such as the lower incisor, lower canine, or pre-molars of the patient, providing additional anchorage points for the device.

In some embodiments, the sublingual dental appliance may be created utilizing a detailed, accurate impression of the patient's lower jaw. To create the impression, orthodontic bands may first be applied to the appropriate teeth of the user, which in some embodiments may be the first lower molars of the user. Application of orthodontic bands is known in the art, the application of which is used to anchor a device to the teeth or to secure an archwire to the molars. The bands are typically made of stainless steel, and may be temporarily cemented to the teeth with cement designed for use with orthodontic bands. The bands, in turn, have attachment mechanisms that allow for application of further dental devices.

Polystyrene molding material is then placed over the lower first molars and applied bands. A cooling element, such as air or water, may be applied over the impressionable polystyrene molding material, causing the material to turn into an opaque, semi-rigid form. While the polystyrene molding material is in place on the lower molars, an impression tray may be sized to the lower arch and placed beneath the ventral (i.e., bottom) surface of the tongue. The impression tray may be modified by cutting into a U-shaped tray, such that the tray may be applied appropriately in the lower jaw. Impression putty, such as Vinyl Polysiloxane (PVS) putty may then be added to the tray. Lastly, the tray and impression putty is applied underneath the tongue, with the material allowed to set for an appropriate period of time.

In some embodiments, the tray and putty, containing an impression of the patient's sublingual area of the jaw, may then be sprayed with alginate adhesive and re-applied to the patient. The alginate impression mixture may then be allowed to set to create an additional detailed impression of the patient.

The tray and previous polystyrene molding material may then both be removed from the mouth and added to a final impression mold. The impression may then be covered with dental stone and allowed to set, providing a stone model for creation of the tailored sublingual dental appliance.

Turning now to FIGS. 1 to 4, an embodiment of a sublingual dental appliance 10 featured in the mandible and applied to the lower dental arch 50 of a patient is shown. The sublingual dental appliance 10 includes a curved frame 11 generally shaped to align with the curvature of the lower dental arch 50 of the patient. In an embodiment, the curved frame 11 forming the base of the sublingual dental appliance 10 may be a lingual arch. The curved frame or lingual arch 11 may be comprised of wire or stainless steel in a preferred embodiment, or may be comprised of other suitable materials for inclusion in a patient's mandible.

Figure 1:
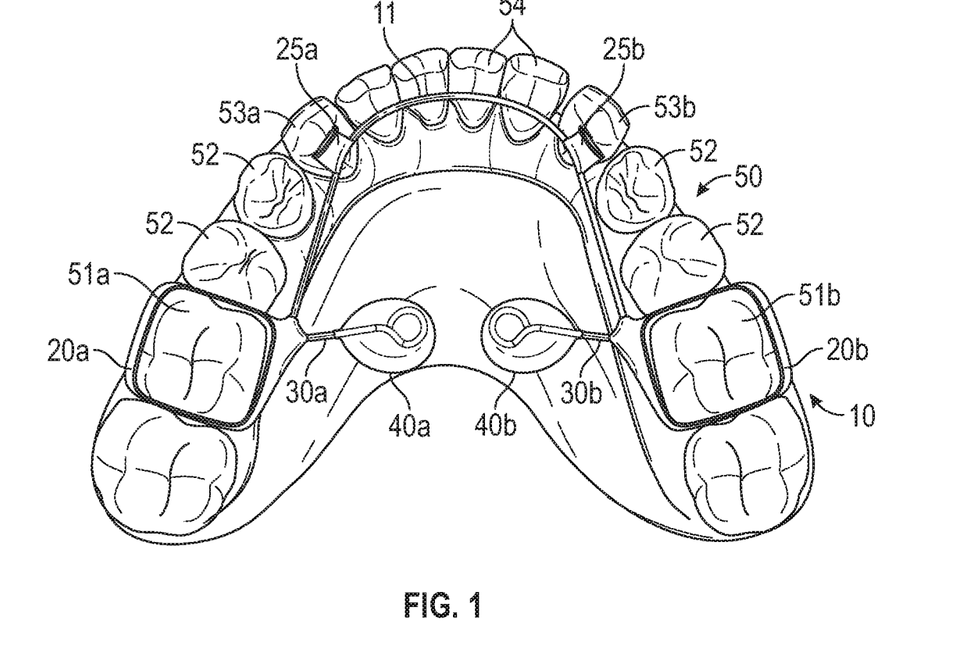
FIG. 1 is a perspective view of a sublingual dental appliance positioned in a mandible, taken in the anterior direction, according to an embodiment of the present disclosure.
Figure 2:
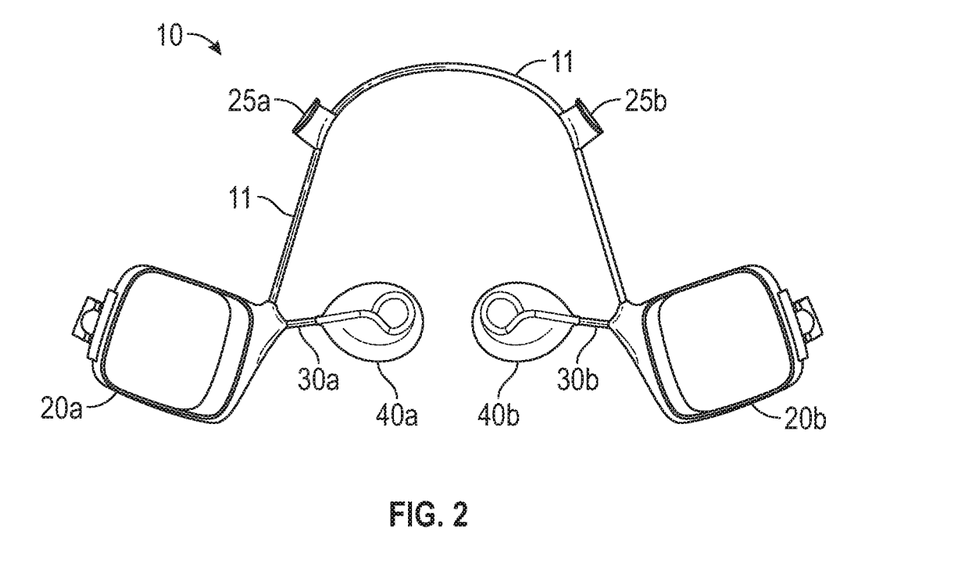
FIG. 2 is a top view of the sublingual dental appliance shown in FIG. 1.
Figure 3:
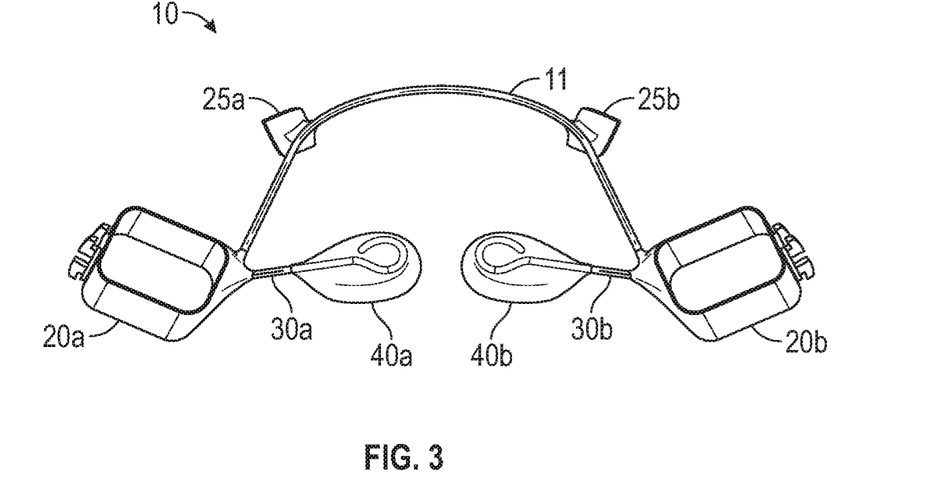
FIG. 3 is a rear perspective view of the sublingual dental appliance shown in FIG. 1.
Figure 4:
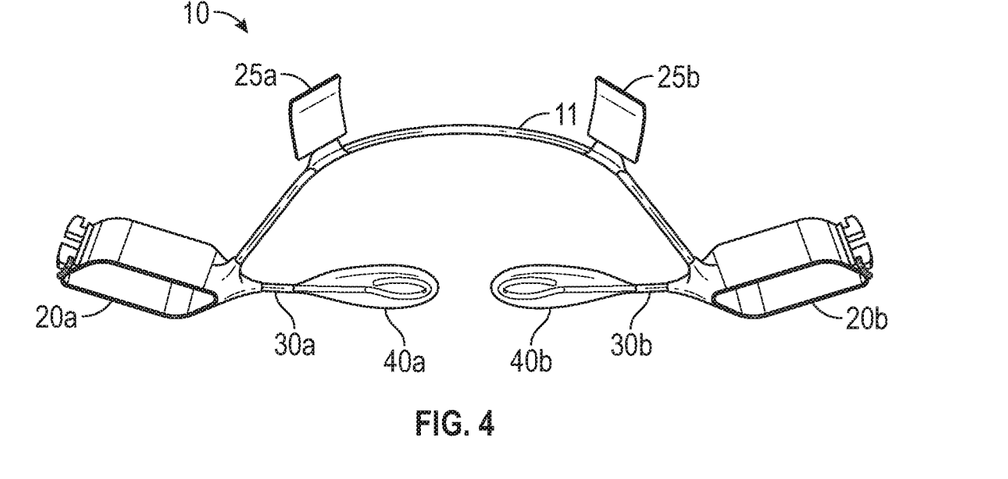
FIG. 4 is a front perspective view of the sublingual dental appliance shown in FIG. 1.

Curved frame 11 includes a pair of securing bands 20a, 20b featured at opposite ends of the curved frame 11. As shown in FIG. 1, curved frame 11 may be of sufficient length such that securing bands 20a, 20b would be configured for securing to the lower molar teeth 51a, 51b of the dental arch 50 of the patient. Although dental arch 50 is depicted as featuring a full set of molar teeth 51, premolars 52, canines 53, and incisors 54, it may be understood that in some applications, dental arch 50 may not include all pictured teeth, or may include implants in place of the pictured teeth. It is contemplated that securing bands 20a, 20b may be configured for securing to any appropriate element of the dental arch 50 of the patient, whether it be the molars, premolars, implants, and so forth, of the patient.

Securing bands 20a, 20b may have the general configuration of a squared ring, as shown in FIGS. 1 to 4, in a shape generally appropriate for application to the selected teeth or implants of the patient. Securing bands 20a, 20b may be present in variable sizes, such that the securing bands 20a, 20b are configured to appropriately secure to the particular element of the lower dental arch 50 of the patient, as discussed in more detail below. In some embodiments, securing bands 20a, 20b may be comprised of stainless steel. In use, as shown in FIG. 1, securing bands 20a, 20b may be cemented in the appropriate position of the lower dental arch 50 by dental cement. Dental cement maybe comprised of, for example and without limitation, glass ionomer cement suitable for securing the securing bands 20a, 20b to the dental arch 50.

In certain embodiments, curved frame 11 may feature additional securing elements 25a, 25b that, in conjunction with the securing bands 20a, 20b, provide additional anchorage for the sublingual dental appliance 10 when in use. Securing elements 25a, 25b may be placed along the curved frame 11 in a position generally corresponding to the canine teeth 53a, 53b of the end user, as shown in FIG. 1. Depending on the configuration of the particular dental arch 50 of the end user, the securing elements 25a, 25b may alternatively be placed in a position generally corresponding to the incisor teeth 54 of the user, or at any other point or points along the lower dental arch 50. In some embodiments, more than two securing elements 25a, 25b may be provided. Securing elements 25a, 25b, when in use, may be secured to the appropriate area of the lower dental arch 50 by appropriate cementing techniques.

Sublingual dental appliance 10 further includes a pair of positioning arms 30a, 30b generally extending from curved frame 11 in the area of the securing bands 20a, 20b in the lingual direction, towards the tongue. Positioning arms 30a, 30b may be comprised of any adjustable material that allows for movement and adjustment without breakage. For example, as shown in FIGS. 1 to 4, positioning arms 30a, 30b may be comprised of the same materials comprising the curved frame or lingual arch 11 and securing bands 20a, 20b. In some embodiments, positioning arms 30a, 30b may be comprised of stainless steel. In some embodiments, positioning arms 30a, 30b may be approximately 0.036 inches (one millimeter) in width and approximately five millimeters in length.

As shown in FIGS. 1 to 4, some embodiments of positioning arms 30a, 30b may feature arms extending from the curved frame 11 in a substantially straight manner, such that the positioning arms 30a, 30b each extend from the curved frame 11 at an angle between approximately 40 degrees to 80 degrees to the curved frame. For example and without limitation, the positioning arms 30a, 30b may extend from curved frame 11 at an angle of approximately 45 degrees.

Figure 5:
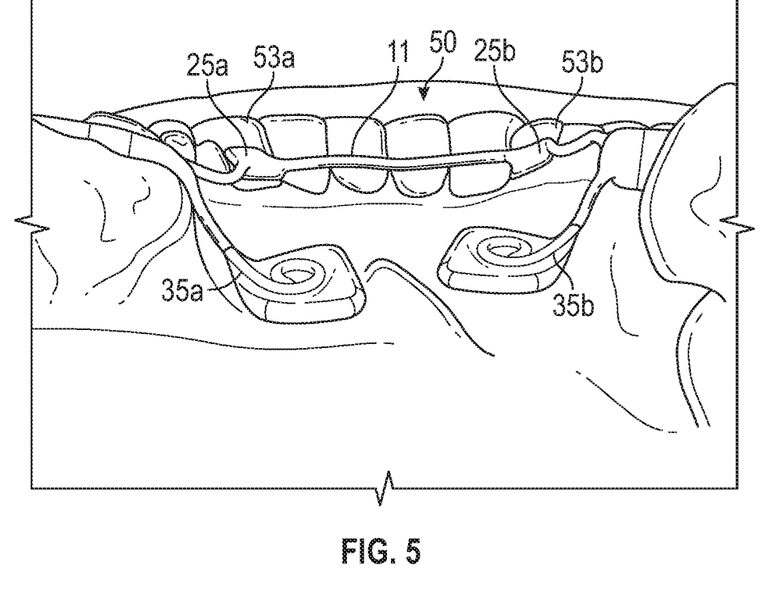
FIG. 5 is a perspective view of a sublingual dental appliance positioned in a mandible, taken in the anterior direction, featuring curved positioning arms, according to an embodiment of the present disclosure.

As shown in FIG. 5, alternate embodiments of sublingual dental appliance 10 may feature a pair of curved positioning arms 35a, 35b. In the embodiment illustrated in FIG. 5, curved positioning arms 35a, 35b may initially extend from the securing bands 20a, 20b along the lingual side of the lower dental arch 50, in the distal direction (for example, towards additional molar teeth of the dental arch 50). Curved positioning arms 35a, 35b may then curve inward in a lingual direction, towards the dental midline of the lower dental arch. Curved positioning arms 35a, 35b, like the corresponding straight positioning arms 30a, 30b, may be comprised of any material suitable for adjustment between a variety of positions during treatment, as discussed in more detail below.

As shown in FIGS. 1 to 5, the ends of positioning arms 30a, 30b (or curved positioning arms 35a, 35b) are each provided with an adjustment pad 40a, 40b. Adjustment pads 40a, 40b may, in some embodiments, be comprised of an acrylic material. In other embodiments, adjustment pads 40a, 40b may be comprised of an alternative plastic material, or glass, or any combination thereof that is suitable for long-term insertion into a patient's mouth and mandible. As shown in FIGS. 1 to 5, adjustment pads 40a, 40b may have a round or ovular configuration. However, alternate embodiments of the sublingual dental appliance 10 may feature adjustment pads 40a, 40b in a variety of shapes, such as square, diamond, triangular, and so forth. Adjustment pads 40a, 40b may be of any shape and configuration such that they fit appropriately into the mandible of the end user and may be supported by its corresponding positioning arm 30a, 30b or 35a, 35b.

When sublingual dental appliance 10 is in use, as shown, for example, in FIG. 7, positioning arms 30a, 30b and adjustment pads 40a, 40b are featured in the mandible below the ventral surface of the tongue. Due to the position of the adjustment pads 40a, 40b, the adjustment pads 40a, 40b apply an upward pressure to the ventral, or bottom, surface of the tongue, generally guiding the tongue upward to an appropriate position in the mouth. For patients experiencing tongue thrust or OMD, the normal position of the tongue is pressed against the lingual or back surface of the teeth; however, with use of adjustment pads 40a, 40b, the tongue is guided into a better relationship with the palate of the mouth. In particular, the tongue may be guided to rest against the superior portion of the palate, or the hard palate, during use and rest of the tongue. Adjustment pads 40a, 40b and positioning arms 30a, 30b may be configured in the lower dental arch 50 such that the tongue is not forced to constantly remain pressed against the hard palate. Rather, the tongue may be simply guided to be proximate to the palate during function and rest, rather than traversing the palate and instead pushing against the lingual surface of the teeth of the patient.

Figure 6:
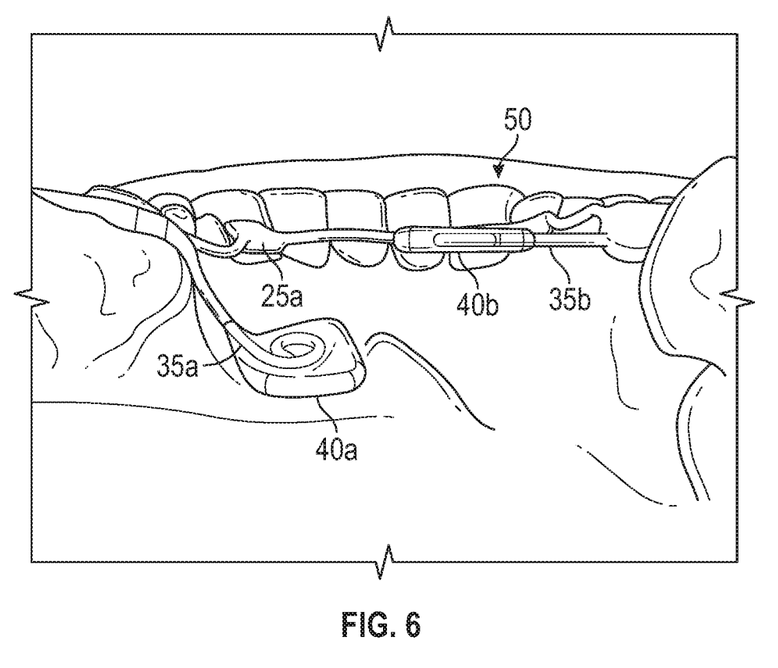
FIG. 6 is a perspective anterior view of the sublingual dental appliance shown in FIG. 5, with the wires in an adjusted position.
Figure 7:
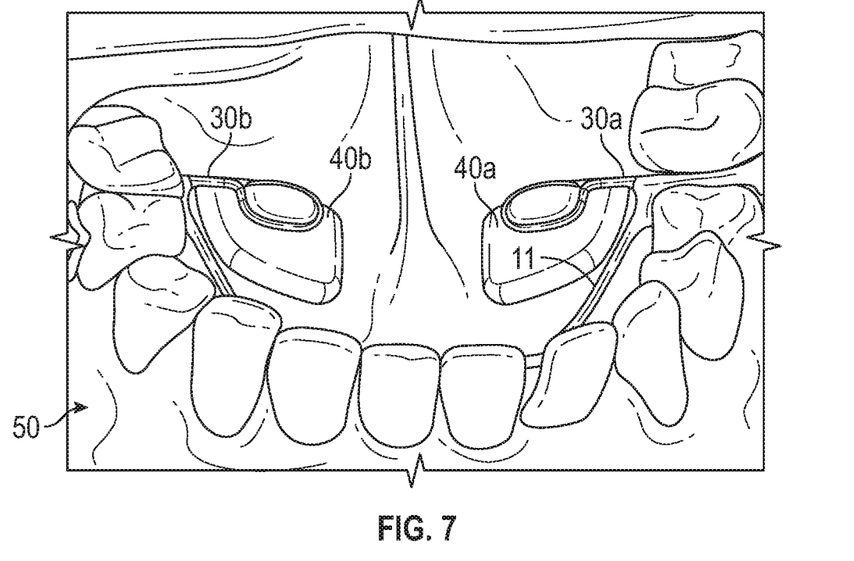
FIG. 7 is a perspective posterior view of a sublingual dental appliance with adjusted positioning wires, according to an embodiment of the present disclosure.

Referring now to FIGS. 6 and 7, adjustment of the positioning arms 30a, 30b or 35a, 35b is shown. Adjustment of positioning arms 35a, 35b may, for instance, be desired in situations wherein the patient begins treatment with only a slight upwards angle of the positioning arms 35a, 35b. During this initial application of the sublingual dental appliance 10 or early stages of treatment, it may be desirable to impart only a gentle pressure to the tongue for the comfort of the patient. However, as the tongue responds to the training of the sublingual dental appliance 10 during treatment, it may be desirable to increase the pressure against the tongue and guide it more definitively to the appropriate region of the palate. In such a scenario, the angle of positioning arms relative to the tongue may be decreased, resulting in additional pressure against the tongue. Additionally or in the alternative, the positioning of the positioning arms 35a, 35b and adjustment pads 40a, 40b may be desired if the tongue is not responding to treatment, and the adjustment pads 40a, 40b need to be shifted to apply pressure to a more appropriate portion of the tongue. Additionally or in the alternative, if the initial pressure against the tongue is too severe on the patient, positioning arms 35a, 35b and adjustment pads 40a, 40b may be angled slightly away from the initial position, such that pressure on the patient is decreased until the next stage of treatment.

By providing flexible positioning arms 30a, 30b and 35a, 35b, such adjustment may be effected without requiring removal of the dental sublingual dental appliance 10 from the patient and subsequent reinsertion into the patient's mandible. Instead, positioning arms 30a, 30b are movable between its first fixed position to a second or more fixed positions during treatment, while still secured or cemented to the patient's lower dental arch. At the same time, positioning arms 30a, 30b are rigid enough to ensure continuous treatment and pressure against the tongue, such that the positioning arms 30a, 30b will not be bent out of position during casual interaction between the tongue and appliance.

Figure 8:
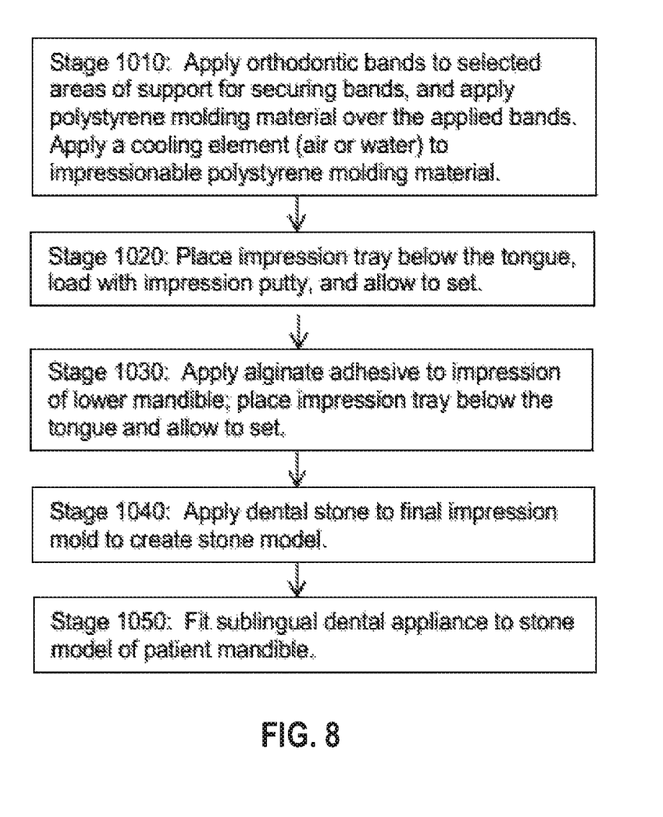
FIG. 8 is a flowchart depicting the method of preparing a sublingual dental appliance, according to an embodiment of the present disclosure.
Figure 9:
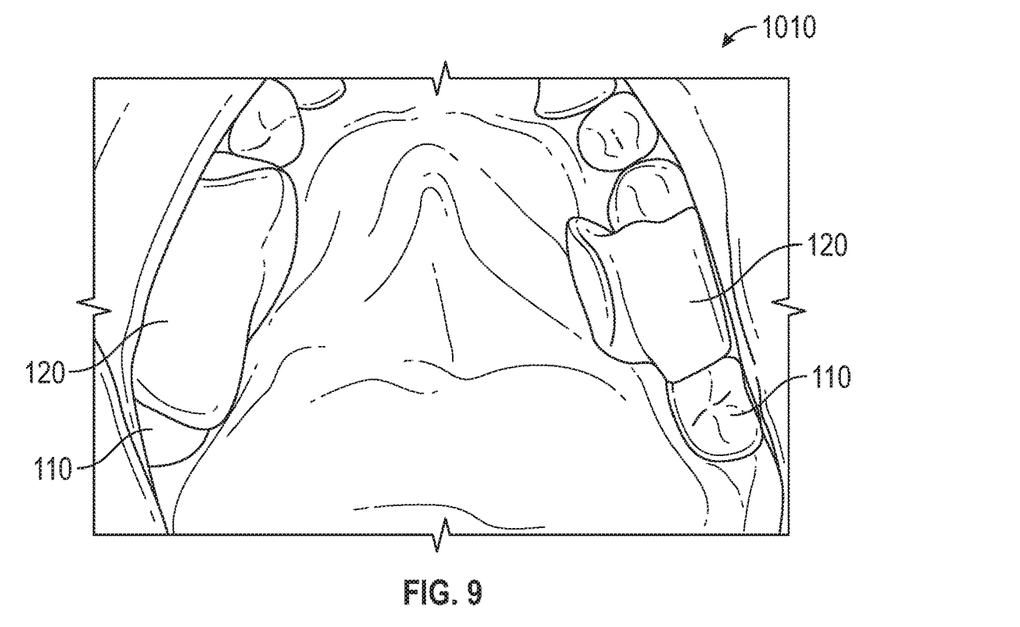
FIG. 9 illustrates the first step in the method of preparing the sublingual dental appliance described in FIG. 8.

Referring now to FIG. 8, a method of manufacturing the sublingual dental appliance 10 is shown. In stage 1010 of the method outlined in FIG. 8, as shown in FIG. 9, orthodontic bands (not shown) may first be applied to the teeth selected for support of the securing bands. In some embodiments, orthodontic bands may be applied to a first and second set of lower molars 110 of the patient. However, it may be understood that, as discussed above, securing bands may alternatively be configured for fixture to premolars, canines, incisors, or implants featured in the lower dental arch, as desired. Upon application of the orthodontic bands to the selected teeth or implants 110 of the user, polystyrene molding material 120 is placed over the applied bands. A cooling element, such as air or water, may be applied over the impressionable polystyrene molding material 120, causing the material to transform into an opaque, semi-rigid form.

Figure 10:
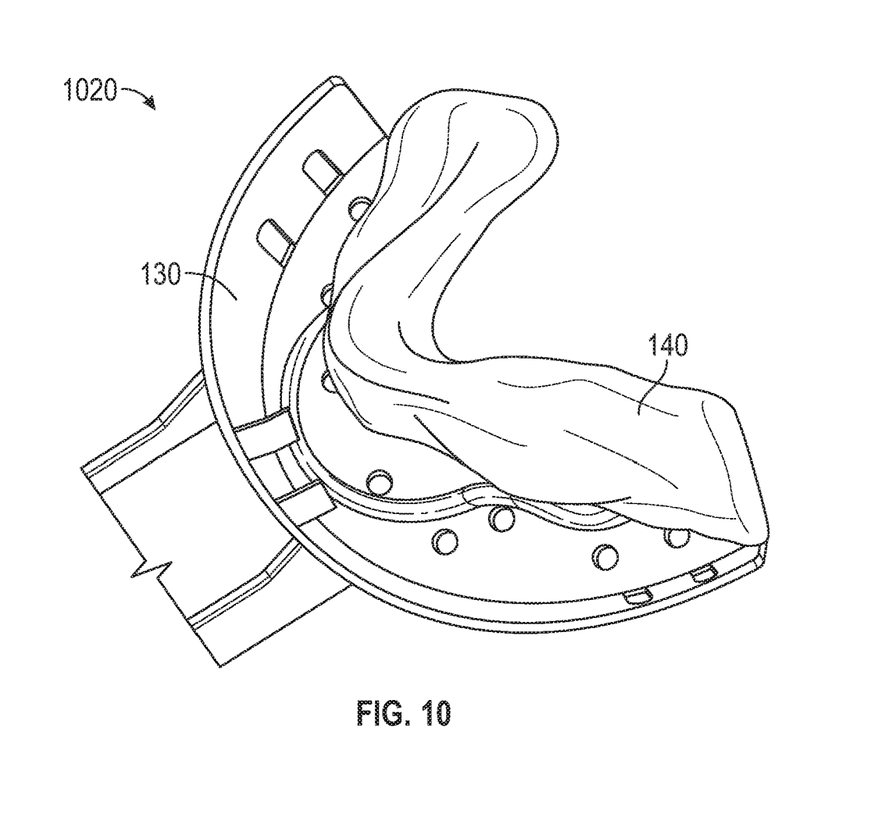
FIG. 10 illustrates the second step in the method of preparing the sublingual dental appliance described in FIG. 8.

In stage 1020 of the method outlined in FIG. 8, as shown in FIG. 10, an impression tray 130 is created for application to the lower dental arch and mandible of the patient. Impression tray 130 is sized to the lower arch of the user and may, in some embodiments, be sized in the general shape of a "U" for ease of application to the mandible. Impression tray 130 is then placed below the tongue. Impression putty 140 is added to the impression tray 130. In some embodiments, impression putty 140 may be Vinyl Polysiloxane (PVS) putty. Impression tray 130 and impression putty 140 are allowed to set while applied in the mandible of the patient, underneath the tongue.

Figure 11:
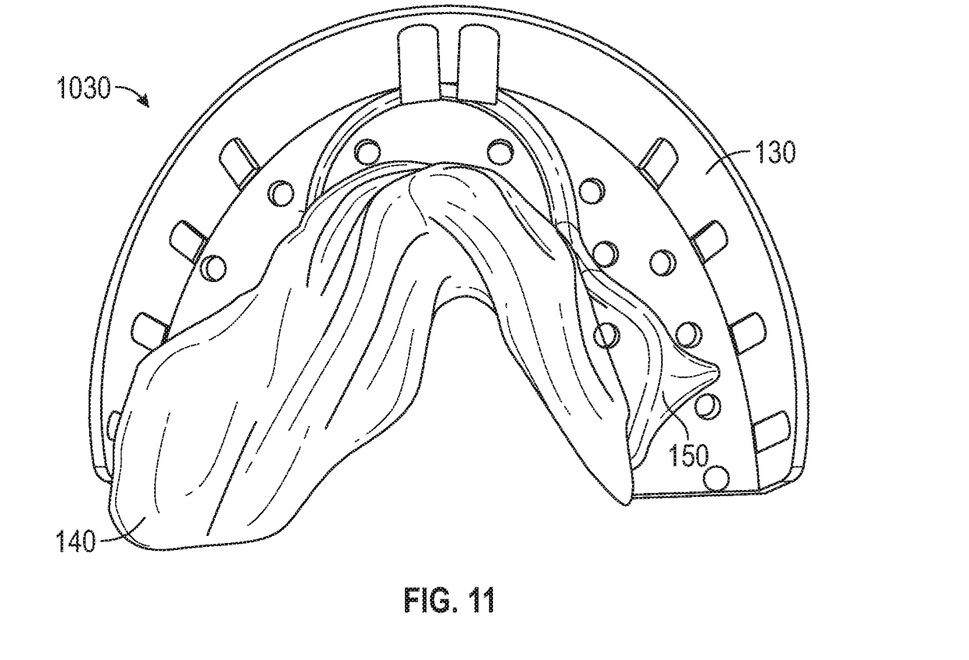
FIG. 11 illustrates the third step in the method of preparing the sublingual dental appliance described in FIG. 8.

Upon removal, as outlined in stage 1030 of FIG. 8 and as shown in FIG. 11, impression tray 130 and impression putty 140 contain an initial impression of the patient's lower dental arch and sublingual area of the jaw. Impression tray 130 and impression putty 140 may then be applied with a layer of alginate adhesive 150. The layer of alginate adhesive 150 may be applied via spray or brush to the impression tray 130 and impression putty 140. The impression tray 130, now containing both the impression putty 140 with the initial impression of the user and the additional coating of alginate adhesive 150, may then be re-applied to the patient, again below the tongue within the lower mandible. The alginate impression mixture may then be allowed to set, resulting in a detailed impression of the patient.

Figure 12:
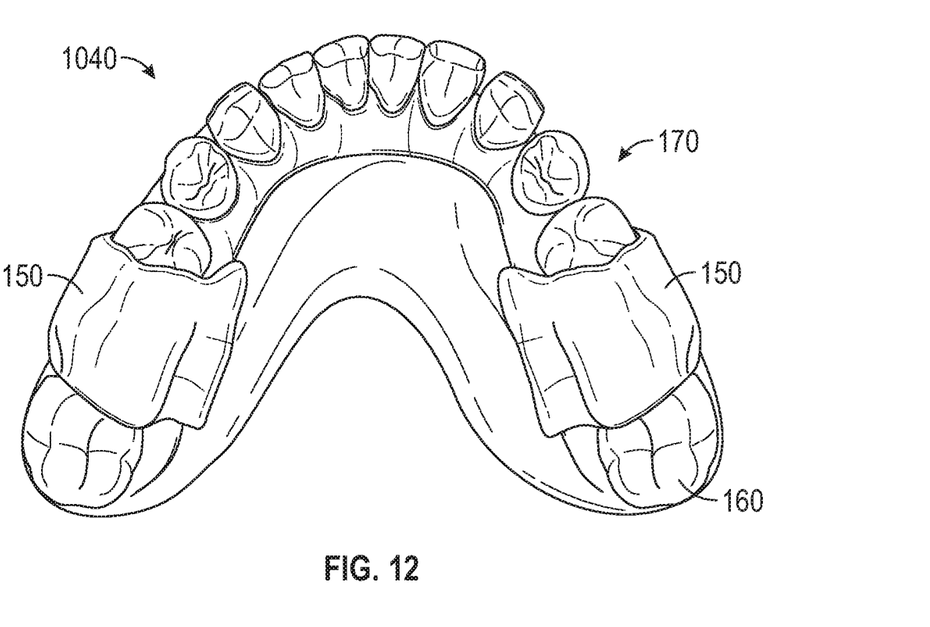
FIG. 12 illustrates the fourth step in the method of preparing the sublingual dental appliance described in FIG. 8.
Figure 13:
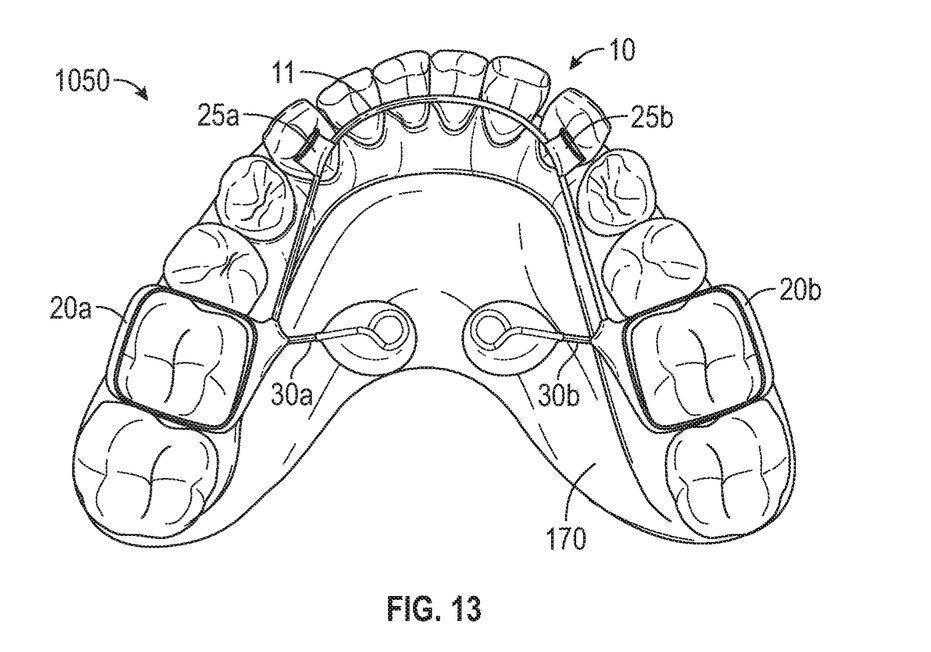
FIG. 13 illustrates the fifth step in the method of preparing the sublingual dental appliance described in FIG. 8.

In step 1040 of the method outlined in FIG. 8, shown in FIG. 12, the impression tray 130 may be removed from the mouth and added to a final impression mold. The impression may be covered with dental stone 160 and allowed to set, providing a stone model 170 for creation of a sublingual dental appliance 10 tailored to the unique features of the patient. For example, as shown in step 1050 of the method outlined in FIG. 8, shown in FIG. 13, sublingual dental appliance 10 may be created directly on stone model 170 to ensure curved frame 11, securing bands 20a, 20b, securing elements 25a, 25b, and positioning arms 30a, 30b are each configured in the appropriate position for the user's particular lower dental arch.

While the embodiments of the present invention are described with reference to various implementations and exploitations, it will be understood that these embodiments are illustrative and that the scope of the inventions is not limited to them. Many variations, modifications, additions, and improvements are possible. The above description should therefore not be construed as limiting, but merely as exemplifications of particular embodiments.

What is claimed is:

1. A dental appliance, comprising:
   a curved frame;
   a securement mechanism attached to the curved frame and configured to attach to a tooth; and
   a positioning arm extending from the curved frame and configured to apply an upward or posterior pressure against a ventral surface of a tongue; wherein the positioning arm is adjustable such that it is movable between a first fixed position and a second fixed position, further comprising an adjustment pad secured to the positioning arm, wherein the adjustment pad is configured to apply an upward or posterior pressure against a ventral surface of a tongue.

2. The dental appliance of claim 1, wherein the positioning arm and the second positioning arm are substantially straight and extend from the curved frame at an angle approximately 45 degrees from the curved frame.

3. The dental appliance of claim 1, wherein the positioning arm and the second positioning arm have a curved configuration.

4. The dental appliance of claim 1, wherein the adjustment pad and the second adjustment pad are comprised of an acrylic material.

5. The dental appliance of claim 1, wherein the positioning arm and the second positioning arm each have a width with a dimension of approximately one millimeter and a length with a dimension of approximately five millimeters.

6. A dental appliance, comprising:
- a lingual arch configured to align with a lower dental arch of a patient;
- a first securing band positioned at a first end of the lingual arch, the first securing band configured to attach to at least a first tooth of the lower dental arch, and a second securing band positioned at a second end of the lingual arch, the second securing band configured to attach to at least a second tooth of the lower dental arch;
- a first positioning arm extending from the lingual arch and a second positioning arm extending from the lingual arch in a position opposite the first positioning arm; and
- a pair of adjustment pads, the first adjustment pad secured to the first positioning arm and the second adjustment pad secured to the second positioning arm;
- wherein the first positioning arm, the first adjustment pad, the second positioning arm, and the second adjustment pad are configured to be positioned below a ventral surface of a tongue of the patient;
- wherein the first adjustment pad and the second adjustment pad are each configured to apply an upward or posterior pressure against the ventral surface of the tongue to position the tongue in a superior portion of a palate of the patient; and
- wherein the first positioning arm and the second positioning arm are adjustable and are each movable between a first fixed position and at least a second fixed position.

7. The dental appliance of claim 6, wherein the first securing band is configured to attach to a first lower molar tooth and the second securing band is configured to attach to a second lower molar tooth.

8. The dental appliance of claim 6, wherein the first securing band and the second securing band are each configured to attach to one of an implant or a tooth of the patient.

9. The dental appliance of claim 6, wherein the first positioning arm and the second positioning arm each extend from the lingual arch in a substantially straight line at an angle approximately 45 degrees to the lingual arch.

10. The dental appliance of claim 6, wherein the first positioning arm and the second positioning arm each extend from the lingual arch in a curved configuration.

11. The dental appliance of claim 6, wherein the first securing band and the second securing band are configured to attach to the at least first and second teeth of the lower dental arch by dental cement.

12. The dental appliance of claim 6, further comprising a first securing element and a second securing element, the first securing element and the second securing element configured to be cemented to a third tooth and a fourth tooth, respectively.

* * * * *